United States Patent [19]

Paulus et al.

[11] Patent Number: 5,538,665
[45] Date of Patent: Jul. 23, 1996

[54] PROCESS FOR STABILIZING A HYDROFLUOROALKANE AND COMPOSITIONS COMPRISING AT LEAST ONE HYDROFLUOROALKANE

[75] Inventors: Mireille Paulus, Brussels; Pierre Barthelemy, Pietrebais, both of Belgium

[73] Assignee: Solvay (Société Anonyme), Brussels, Belgium

[21] Appl. No.: 21,067

[22] Filed: Feb. 23, 1993

[30] Foreign Application Priority Data

Mar. 2, 1992 [BE] Belgium ............................... 09200206

[51] Int. Cl.⁶ .................................................... C11D 7/30
[52] U.S. Cl. ...................... 252/67; 252/307; 252/364; 510/401; 510/255; 510/258; 510/412
[58] Field of Search ................. 252/67, 68, 153, 252/171, 162, DIG. 9; 568/701

[56] References Cited

U.S. PATENT DOCUMENTS

| | | | |
|---|---|---|---|
| 4,584,174 | 1/1990 | Swan et al. | 252/171 |
| 4,803,009 | 2/1989 | Gorski | 252/171 |
| 4,842,764 | 6/1989 | Lund et al. | 252/171 |
| 4,863,630 | 9/1980 | Swan et al. | 252/177 |
| 5,120,461 | 6/1992 | Logsdon et al. | 252/162 |
| 5,122,294 | 6/1992 | Logsdon et al. | 252/162 |

FOREIGN PATENT DOCUMENTS

| | | |
|---|---|---|
| 562820 | 10/1932 | Germany . |
| 7222562 | 6/1972 | Japan . |
| 1132539A | 5/1989 | Japan . |
| 2157234A | 6/1990 | Japan . |
| 2273632A | 11/1990 | Japan . |
| 9113969 | 9/1991 | WIPO . |
| WO9118852 | 12/1991 | WIPO . |

*Primary Examiner*—Paul Lieberman
*Assistant Examiner*—Necholus Ogden
*Attorney, Agent, or Firm*—Spencer & Frank

[57] ABSTRACT

Hydrofluoroalkanes are effectively stabilized against degradation caused by Lewis acids by addition of 0.001 to less than 0.1% by weight of at least one $C_1$–$C_2$ alcohol and/or of 0.001% to 0.5% of a $C_5$–$C_6$ unsaturated hydrocarbon.

4 Claims, No Drawings

PROCESS FOR STABILIZING A HYDROFLUOROALKANE AND COMPOSITIONS COMPRISING AT LEAST ONE HYDROFLUOROALKANE

The present invention relates to the stabilisation of hydrofluoroalkanes, and more particularly to the stabilisation of 1,1-dichloro-1-fluoroethane.

Being suspected of attacking the stratospheric ozone layer, completely halogenated chlorofluorocarbons (CFCs) are gradually being replaced with various substitutes, especially partially halogenated fluorocarbons and chlorofluorocarbons, generally referred to by the generic term of hydrofluoroalkanes (HFAs). For example, 1,1-dichloro-1-fluoroethane (HFA-141b) is a hydrofluoroalkane which turns out to be an advantageous substitute for some CFCs, especially as blowing agent for polymer foams or as solvent.

It is generally recognised that hydrofluoroalkanes must be stabilised to avoid any risk of degradation in storage or use, more particularly when they are employed as solvents. A potential degradation of these compounds is linked with their possible hydrolysis, causing the formation of HCl. When they are employed as a solvent for degreasing metal articles, the risk of degradation is increased because of the possible catalytic action of these metals on the hydrolysis reaction.

The Showa-Denko examined Patent Application JP-B-72/22,562 teaches, in its general principle, the stabilisation of bromochlorofluorinated hydrocarbons employed as anaesthetics, by addition of 0.01 to 1% by weight of a lower alkanol.

The Asahi unexamined Patent Application JP-A-02/273,632 discloses azeotropic or pseudoazeotropic compositions containing from 99.9 to 90% of 1,1-dichloro-1-fluoroethane and from 0.1 to 10% of methanol or ethanol.

In Allied-Signal U.S. Pat. No. 4,824,764 it is taught, however, that a solvent composition based on chlorofluorocarbon and on a lower alkanol is highly corrosive towards certain metal surfaces.

The Asahi unexamined Patent Application JP-A-01/132,539 teaches a process for heat stabilisation of azeotropic solvent compositions containing 73.5% of 1,2-dichloro-1-fluoroethane and 26.5% of methanol, by addition of various stabilisers.

Solvay Patent Application WO 91/18,852 teaches that 1,1-dichloro-1-fluoroethane can undergo degradation in the presence of at least 10 ppm of Lewis acids. However, it has now been noted that even smaller quantities of Lewis acids, in particular of the metal halide type, can induce a considerable degradation of hydrofluoroalkanes such as 1,1-dichloro-1-fluoroethane. Thus, from 2 to 3 ppm of iron chloride dissolved in 1,1-dichloro-1-fluoroethane are sufficient for very quickly unacceptably damaging the quality of the product, even at room temperature. In addition, it has also been observed that hydrofluoroalkanes which contain traces of Lewis acids of metal halide type turn out to be highly corrosive to metal surfaces.

The invention is aimed at overcoming the disadvantages described above by providing a process for the stabilising of hydrofluoroalkanes which, in particular, avoids a degradation of the latter by Lewis acids of metal halide type. It is also aimed at providing, as a new product, the hydrofluoroalkane thus stabilised, which is noncorrosive to metal surfaces.

The subject of the present invention is consequently a process for stabilising a hydrofluoroalkane against degradation caused by Lewis acids of metal halide type, according to which at least one alcohol and/or at least one unsaturated hydrocarbon are added as stabiliser to the said hydrofluoroalkane, which is characterised in that the alcohol is chosen from methanol, ethanol and ethylene glycol and the unsaturated hydrocarbon from $C_5$–$C_6$ alkenes, and in that the said alcohol is used in a quantity by weight of at least approximately 0.001% and less than 0.1% of the weight of the hydrofluoroalkane and the said unsaturated hydrocarbon in a quantity of at least approximately 0.001% and less than approximately 0.5 % of the weight of the hydrofluoroalkane.

Hydrofluoroalkane is generally intended to denote any saturated halogenated hydrocarbon, of acyclic or alicyclic type containing at least one hydrogen atom and at least one fluorine atom. These hydrofluoroalkanes may or may not in addition contain one or a number of chlorine or bromine atoms. They preferably do not contain any bromine.

The hydrofluoroalkanes as defined generally contain from 1 to 6 carbon atoms.

Lewis acids of metal halide type are intended to denote metal halides which have the properties of Lewis acids, that is to say those whose electronic structure is such that they are capable of accepting electrons from basic reactants. Such Lewis acids are especially $FeCl_3$, $AlCl_3$, $SbCl_5$, $SbCl_3$, $SnCl_4$, $TiCl_4$, $BCl_3$ and $BF_3$.

It has been observed, very surprisingly, that the addition in a quantity of less than 0.1% of an alcohol chosen from methanol, ethanol and ethylene glycol to a hydrofluoroalkane inhibits any degradation of the product in the presence of Lewis acids of metal halide type, without making this product corrosive to metal surfaces, whereas, on the other hand, it has been observed that other alcohols, such as isopropanol, even when they are employed in increased quantities, greater than 0.1% of the weight of the hydrofluoroalkane, are powerless to inhibit the degradation of hydrofluoroalkanes by Lewis acids of metal halide type.

Methanol and ethylene glycol are preferred.

Methanol is the alcohol very particularly preferred.

In the process according to the invention the alcohol is generally added in a quantity of at least 0.001% and less than 0.1% of the weight of the hydrofluoroalkane to be stabilised.

Quantities which are especially recommended for the alcohol are those greater than or equal to 0.005% of the weight of the hydrofluoroalkane, preferably greater than or equal to 0.008%, and those less than or equal to 0.09% of the weight of the hydrofluoroalkane, preferably less than or equal to 0.08%.

The unsaturated hydrocarbons which can be employed in the process according to the invention are $C_5$–$C_6$ alkenes. Alkenes are intended to denote aliphatic alkenes and cycloalkenes. Examples which may be mentioned are methylbutenes, dimethylbutenes, pentenes, methylpentenes, hexenes, cyclopentene, cyclohexene and methylcyclopentene. Particularly advantageous unsaturated hydrocarbons are especially 2-methyl-2-butene, 2-methyl-1-butene, 3-methyl-1-butene, 2-ethyl-1-butene, 1-pentene, 2-pentene, 2-methyl-1-pentene, 2-methyl-2-pentene, 3-methyl-1-pentene, 3-methyl-2-pentene, 4-methyl-1-pentene, 1-hexene, 2-hexene and 3-hexene. Among these unsaturated hydrocarbons 2-methyl-2-butene, 2-methyl-1-butene and 3-methyl-1-butene and mixtures thereof are preferred. Very good results have been obtained with industrial 2-methyl-2-butene, usually called amylene, which may contain a little 2-methyl-1-butene.

In the process according to the invention the unsaturated hydrocarbon is generally added in a quantity of at least 0.001% and less than 0.5% of the weight of the hydrofluoroalkane to be stabilised.

The unsaturated hydrocarbon(s) is (are) preferably added in a quantity of approximately 0.005 to approximately 0.25% of the weight of hydrofluoroalkane.

In a preferred embodiment of the process according to the invention, at least one alcohol and at least one unsaturated hydrocarbon are jointly added to the hydrofluoroalkane to be stabilised.

Unexpectedly, the joint addition to a hydrofluoroalkane of at least one alcohol chosen from methanol, ethanol and ethylene glycol and of at least one unsaturated hydrocarbon chosen from $C_5$–$C_6$ alkenes, in chosen quantities defined above, stabilises the hydrofluoroalkane particularly effectively. The existence of a synergy between the alcohol and the unsaturated hydrocarbon makes it possible to obtain very good stabilisation results by the addition of approximately 0.001% to approximately 0.075% of alcohols, preferably methanol, and of approximately 0.001% to approximately 0.5% of unsaturated hydrocarbons, preferably amylene. By way of illustration, a very good inhibition of the degradation of 1,1-dichloro-1-fluoroethane in the presence of Lewis acids of metal halide type can be obtained by adding methanol in a quantity of approximately 0.005% to approximately 0.06% of the weight of 1,1-dichloro-1-fluoroethane and of amylene in a quantity of approximately 0.005% to approximately 0.25% of the weight of 1,1-dichloro-1-fluoroethane, the simultaneous presence of methanol and of amylene giving rise to a synergistic effect on the stability of 1,1-dichloro-1-fluoroethane.

The process according to the invention can be applied for stabilising any hydrofluoroalkane liable to be in contact with Lewis acids of metal halide type either during storage, which is generally performed in liquid form, or during its subsequent use in gaseous or liquid form.

The process according to the invention finds an advantageous application for the stabilisation of acyclic or alicyclic hydrofluoroalkanes of general formula $C_aH_bF_cX_d$ in which X is Cl and/or Br, preferably Cl, a is an integer from 1 to 6, b is an integer from 1 to 13, c is an integer from 1 to 13 and d is an integer from 0 to 8, with b+c+d=2a+2 when the compound is acyclic and with b+c+d=2a when the compound is alicyclic. The process is particularly applicable to acyclic compounds corresponding to the above general formula in which X is Cl, a is an integer equal to 1 to 4, b is an integer from 1 to 9, c is an integer from 1 to 9 and d is an integer from 0 to 5. The process is very particularly applicable to acyclic compounds corresponding to the above general formula in which X is Cl, a is an integer equal to 2 or 3, b is an integer from 1 to 6, c is an integer from 1 to 6 and d is an integer from 1 to 4. Hydrofluoroalkanes which can be treated using the process of the invention are especially the compounds of molecular formula $CHClF_2$, $CH_2F_2$, $CH_3CCl_2F$, $CH_3CClF_2$, $CH_3CHF_2$, $CH_3CF_3$, $CH_2FCH_2F$, $CH_2FCHF_2$, $CH_2FCF_3$, $CHF_2CCl_3$, $CHF_2CF_3$, $CHCl_2CF_3$, $CHF_2CHF_2$, $CF_3CHClF$, $CF_3CF_2CHCl_2$, $CF_2ClCF_2CHClF$, $CF_3CH_2CF_2CH_3$ and $CF_3CH_2CH_2CF_3$.

The process according to the invention gives very good results when applied to the stabilisation of 1,1-dichloro-1-fluoroethane. Excellent results are obtained in this case, especially in the presence of Lewis acids of metal halide type, whether present in minuscule quantities, for example of the order of 0.1 mg per kilogram of hydrofluoroalkane, or in larger quantities, for example of the order of several hundred mg per kilogram of hydrofluoroalkane. The process according to the invention gives excellent results when compositions based on 1,1-dichloro-1-fluoroethane are in the presence of a quantity of Lewis acids of metal halide type of between approximately 0.5 and 500 mg per kilogram of hydrofluoroalkane. Very good results are also obtained with the process according to the invention when the composition based on 1,1-dichloro-1-fluoroethane is in contact with large quantities of Lewis acids of metal halide type, of the order of a gram or more of Lewis acids per kilogram of 1,1-dichloro-1-fluoroethane.

Hydrofluoroalkanes stabilised by means of the process according to the invention can be stored for a number of months without special precautions, without being degraded. Their behaviour is not affected in any way whatever by the presence of the alcohol or of the unsaturated hydrocarbon.

Hydrofluoroalkanes stabilised by means of the process according to the invention are suitable for all the conventional uses of hydrofluoroalkanes, for example as cleaning solvent, as blowing agent for polymer foams or as refrigerant fluid, without it being necessary to remove therefrom any trace of Lewis acids of metal halide type, or of taking complex and costly precautions in order to avoid the appearance of such compounds in the storage vessels or in the numerous application devices.

The invention consequently also relates to compositions stabilised against degradation caused by Lewis acids of metal halide type, comprising at least one hydrofluoroalkane and, at least one alcohol and/or an unsaturated hydrocarbon as stabiliser, which are characterised in that the alcohol is chosen from methanol, ethanol and ethylene glycol, in a quantity by weight of at least approximately 0.001% and less than 0.1% of the weight of the hydrofluoroalkane and the unsaturated hydrocarbon from $C_5$–$C_6$ alkenes, in a quantity by weight of at least approximately 0.001% and less than approximately 0.5% of the weight of the hydrofluoroalkane. The alcohol employed as stabiliser is preferably present in a quantity greater than or equal to 0.005% and less than or equal to approximately 0.09% by weight of hydrofluoroalkane. The unsaturated hydrocarbon employed as stabiliser is preferably present in a quantity of approximately 0.005% to approximately 0.25% of the weight of the hydrofluoroalkane.

The alcohol is advantageously chosen from methanol and ethylene glycol, methanol being very particularly preferred. The unsaturated hydrocarbon is advantageously chosen from 2-methyl-2-butene, 2-methyl-1-butene, 3-methyl-1-butene and mixtures thereof.

The hydrofluoroalkane in the compositions according to the invention may be any hydrofluoroalkane described above. It is advantageously 1,1-dichloro-1-fluoroethane.

According to a preferred embodiment of the invention the compositions jointly contain at least one alcohol and at least one unsaturated hydrocarbon in addition to the hydrofluoroalkane.

In an alternative form the compositions according to the invention may also contain other additives which usually accompany the hydrofluoroalkanes. They may also contain other stabilisers.

The following examples illustrate the invention. Examples 1 to 4, 9, 15, 19 and 20, marked R, are given by way of comparison. Examples 5 to 8, 10 to 14, 16 to 18 and 21 to 23 are carried out according to the invention.

EXAMPLES 1–8

1,1-Dichloro-1-fluoroethane was stored at 50° C. in stainless steel gas bottles in the presence of variable quantities of various stabilisers and $FeCl_3$. The main organic impurities present in the 1,1-dichloro-1-fluoroethane initially, and then after 7 days' treatment, were analysed by gas phase chromatography. These impurities are essentially 1-chloro-1-fluoroethylene (VCF), 1,1-dichloroethylene (VC2), 1-chloro-1,1-difluoroethane (HCFC-142b) and 1,1,1-trichloroethane (T111). The fluoride ion content was also measured. The results are listed in Table I below.

EXAMPLES 19–23

1,1-Dichloro-1-fluoroethane of the same purity as that employed for Examples 1 to 8, to which various stabilisers have been added, is refluxed in a round bottom boiler flask supporting a Soxhlet extractor and a condenser, in the presence of metal test pieces, one of which is placed in the boiler, a second one in the Soxhlet extractor and a third in the condenser. The metal test pieces made of Thomas steel have a surface area of 832 $mm^2$ overall. The corrosiveness of the stabilised 1,1-dichloro-1-fluoroethane compositions is evaluated by measuring the weight loss of the test pieces after 7 days. The results are collated in Table III.

TABLE I

| | $FeCl_3$ (g/kg HCFC-141b) | STABILISER (weight % HCFC-141b) | IMPURITIES (mg/kg of the total composition) | | | | |
|---|---|---|---|---|---|---|---|
| | | | VCF | VC2 | HCFC-142b | T111 | fluorides |
| Initial composition | — | — | 1 | 239 | 3 | — | 0.13 |
| Example 1R | 0.012 | — | 47 | 499 | 11 | 690 | 4.2 |
| Example 2R | 1 | — | 99 | 1272 | 357 | 1285 | 22 |
| Example 3R | 1 | isopropanol 0.5 | 2 | 347 | 14 | 155 | 8.7 |
| Example 4R | 1 | methanol 0.1 | 3 | 282 | 3 | 52 | 0.1 |
| Example 5 | 1 | methanol 0.08 | 1 | 228 | 1 | 21 | 0.1 |
| Example 6 | 0.253 | methanol 0.01 | 5 | 203 | 1 | 20 | 0.2 |
| Example 7 | 0.253 | methanol 0.05 | 2 | 202 | 2 | 19 | 0.2 |
| Example 8 | 1 | methanol 0.05 + amylene 0.1 | 1 | 131 | <1 | 9 | 0.3 |

EXAMPLES 9–18

1,1-dichloro-1-fluoroethane of better purity than that employed in Examples 1 to 8 was stored for 7 days at 50° C. in stainless steel gas bottles in the presence of 1 gram of $FeCl_3$ per kilogram of 1,1-dichloro-1-fluoroethane and of variable quantities of various stabilisers.

The results of the analyses are listed in Table II below.

TABLE II

| | STABILISER (weight % HCFC-141b) | IMPURITIES (mg/kg of the total composition) | | | | |
|---|---|---|---|---|---|---|
| | | VCF | VC2 | HCFC-142b | T111 | fluorides |
| Initial composition | — | 1 | 9 | 1 | 12 | <0.01 |
| Example 9R | — | 59 | 389 | 40 | 882 | 91 |
| Example 10 | methanol 0.08 | 4 | 11 | 2 | 14 | 0.4 |
| Example 11 | methanol 0.05 | 2 | 9 | 2 | 13 | 0.7 |
| Example 12 | ethanol 0.08 | 3 | 12 | 1 | 9 | 0.4 |
| Example 13 | ethylene glycol 0.08 | 2 | 8 | 2 | 7 | 0.02 |
| Example 14 | ethylene glycol 0.02 | 2 | 20 | 2 | 36 | 0.1 |
| Example 15R | isopropanol 0.02 | 187 | 297 | 5 | 144 | 20 |
| Example 16 | amylene 0.1 | 5 | 10 | 2 | 13 | 0.5 |
| Example 17 | methanol 0.08 + amylene 0.1 | 2 | 9 | 2 | n.d. | 0.1 |
| Example 18 | methanol 0.05 + amylene 0.1 | 2 | 11 | 2 | 9 | 0.1 |

(n.d. = not determined)

TABLE III

| | Ex.19R | Ex.20R | Ex.21 | Ex.22 | Ex.23 |
|---|---|---|---|---|---|
| Stabiliser (weight % relative to HCFC-141b) | | | | | |
| methanol | 0.5% | 0.1% | 0.05% | 0.01% | 0.05% |
| amylene | — | — | — | — | 0.01% |
| Losses in weight (g/m² day) | | | | | |
| flask | 0.05 | 0 | 0.02 | 0.02 | 0.02 |
| Soxhlet | 0.32 | 0.36 | 0.02 | 0.03 | 0 |
| condenser | 0.17 | 0.02 | 0 | 0.05 | 0 |
| total loss | 0.54 | 0.38 | 0.04 | 0.10 | 0.02 |

We claim:

1. A composition stabilised against degradation caused by a metal halide Lewis acid, comprising 1,1-dichloro-1-fluoroethane and methanol present in a quantity of at least approximately 0.001% and less than 0.1% of the weight of the 1,1-dichloro-1-fluoroethane.

2. The composition according to claim 1, including at least one unsaturated hydrocarbon selected from $C_5$–$C_6$ alkenes, said unsaturated hydrocarbon present in a quantity by weight of at least approximately 0.001% and less than approximately 0.05% of the weight of the 1,1-dichloro-1-fluoroethane.

3. The composition according to claim 1, wherein the alcohol is present in a quantity greater than or equal to 0.005% and less than or equal to approximately 0.09% of the weight of the 1,1-dichloro-1-fluoroethane.

4. The composition according to claim 2, wherein the unsaturated hydrocarbon is selected from the group consisting of 2-methyl-2-butene, 2-methyl-1-butene, 3-methyl-1-butene, and mixtures thereof.

* * * * *